(12) United States Patent
Wiegel et al.

(10) Patent No.: US 12,249,099 B2
(45) Date of Patent: Mar. 11, 2025

(54) SYSTEMS, METHODS, AND DEVICES FOR RECONSTRUCTING A THREE-DIMENSIONAL REPRESENTATION

(71) Applicant: Medtronic Navigation, Inc., Louisville, CO (US)

(72) Inventors: Stephanie Elizabeth Wiegel, Lafayette, CO (US); Aditya R. Dalvi, Broomfield, CO (US); Andrew J. Koert, Golden, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 291 days.

(21) Appl. No.: 17/591,919

(22) Filed: Feb. 3, 2022

(65) Prior Publication Data
US 2023/0281869 A1 Sep. 7, 2023

(51) Int. Cl.
*G06T 7/73* (2017.01)
*A61B 34/30* (2016.01)
*G06T 17/00* (2006.01)

(52) U.S. Cl.
CPC .............. *G06T 7/75* (2017.01); *A61B 34/30* (2016.02); *G06T 17/00* (2013.01); *G06T 2200/08* (2013.01); *G06T 2207/10132* (2013.01); *G06T 2207/20081* (2013.01)

(58) Field of Classification Search
CPC ....... A61B 34/20; A61B 5/055; A61B 8/0841; A61B 34/10; A61B 2034/105; A61B 2034/2051; A61B 8/12; A61B 2090/364; A61B 2034/107; A61B 6/032; A61B 2090/378; A61B 2034/2055; A61B 90/36; A61B 2090/374; A61B 2090/367; A61B 6/12; A61B 17/3403; A61B 2017/3411; A61B 2034/2061; A61B 2090/363
USPC ...................................................... 382/128
See application file for complete search history.

(56) References Cited

U.S. PATENT DOCUMENTS

| | | | |
|---|---|---|---|
| 5,810,008 A | 9/1998 | Dekel et al. | |
| 6,019,724 A | 2/2000 | Gronningsaeter | |
| 6,390,982 B1 | 5/2002 | Bova et al. | |
| 6,685,644 B2 | 2/2004 | Seo et al. | |
| 6,872,179 B2 | 3/2005 | Kamiyama et al. | |

(Continued)

FOREIGN PATENT DOCUMENTS

| | | |
|---|---|---|
| CN | 103777840 | 5/2014 |
| JP | 2011-182983 | 9/2011 |

(Continued)

OTHER PUBLICATIONS

Official Action for U.S. Appl. No. 17/591,904, dated Sep. 7, 2023 16 pages.

(Continued)

*Primary Examiner* — Ajibola A Akinyemi
(74) *Attorney, Agent, or Firm* — Sheridan Ross P.C.

(57) ABSTRACT

Systems, methods, and devices for reconstructing an image is provided. An imaging device may be oriented at one or more poses and an image may be received at each of the one or more poses to form a set of images. Pose information may be received at each of the one or more poses. The set of images and the pose information may be inputted into a reconstruction model to generate a three-dimensional representation of the one or more anatomical elements.

19 Claims, 5 Drawing Sheets

(56) References Cited

U.S. PATENT DOCUMENTS

| | | | |
|---|---|---|---|
| 7,203,277 | B2 | 4/2007 | Birkenbach et al. |
| 7,452,357 | B2 | 11/2008 | Vlegele et al. |
| 8,116,848 | B2 | 2/2012 | Shahidi |
| 9,055,883 | B2 | 6/2015 | Tgavalekos et al. |
| 9,204,863 | B2 | 12/2015 | Kumazawa |
| 9,211,163 | B1 | 12/2015 | Jaramaz et al. |
| 9,471,981 | B2 | 10/2016 | Arai et al. |
| 9,486,162 | B2 | 11/2016 | Zhuang et al. |
| 10,026,191 | B2 | 7/2018 | Accomando et al. |
| 10,383,693 | B2 | 8/2019 | Schmoll et al. |
| 10,568,535 | B2 | 2/2020 | Roberts et al. |
| 10,650,537 | B2 | 5/2020 | O'Connor et al. |
| 10,762,341 | B2 | 9/2020 | Vilsmeier et al. |
| 11,197,722 | B2 | 12/2021 | Tako et al. |
| 11,553,969 | B1 | 1/2023 | Lang et al. |
| 2004/0106869 | A1 | 6/2004 | Tepper |
| 2005/0085717 | A1 | 4/2005 | Shahidi |
| 2005/0261571 | A1 | 11/2005 | Willis et al. |
| 2006/0176242 | A1 | 8/2006 | Jaramaz et al. |
| 2007/0021738 | A1 | 1/2007 | Hasser et al. |
| 2007/0239000 | A1 | 10/2007 | Emery et al. |
| 2007/0276234 | A1 | 11/2007 | Shahidi |
| 2008/0137927 | A1 | 6/2008 | Altmann et al. |
| 2008/0247506 | A1 | 10/2008 | Maschke |
| 2013/0158578 | A1 | 6/2013 | Ghodke et al. |
| 2014/0066766 | A1 | 3/2014 | Stonefield et al. |
| 2015/0130799 | A1 | 5/2015 | Holzer et al. |
| 2015/0320395 | A1 | 11/2015 | Sato |
| 2015/0359517 | A1 | 12/2015 | Tan |
| 2016/0150217 | A1 | 5/2016 | Popov |
| 2018/0263706 | A1 | 9/2018 | Averbuch |
| 2018/0303463 | A1 | 10/2018 | Zanin et al. |
| 2018/0344411 | A1 | 12/2018 | Fahey et al. |
| 2019/0209130 | A1 | 7/2019 | Lieblich et al. |
| 2019/0219693 | A1 | 7/2019 | Lieblich et al. |
| 2019/0262082 | A1 | 8/2019 | Krimsky et al. |
| 2019/0271771 | A1 | 9/2019 | Lieblich et al. |
| 2020/0159313 | A1 | 5/2020 | Gibby et al. |
| 2020/0334897 | A1 | 10/2020 | Oved |
| 2021/0177524 | A1 | 6/2021 | Thienphrapa et al. |
| 2021/0192763 | A1 | 6/2021 | Liu et al. |
| 2021/0196424 | A1 | 7/2021 | Shelton et al. |
| 2021/0386491 | A1 | 12/2021 | Shmayahu et al. |
| 2022/0079675 | A1 | 3/2022 | Lang |
| 2022/0104878 | A1* | 4/2022 | Weiss ............... G16H 20/40 |
| 2022/0189047 | A1* | 6/2022 | Lev-Tov ............. G16H 30/20 |

FOREIGN PATENT DOCUMENTS

| | | |
|---|---|---|
| JP | WO 2009-136461 | 9/2011 |
| KR | 10-2016-0026598 | 3/2016 |
| WO | WO 2008/038283 | 4/2008 |
| WO | WO 2014/174069 | 10/2014 |
| WO | WO 2016/018646 | 2/2016 |
| WO | WO 2016/026053 | 2/2016 |
| WO | WO 2016/082017 | 6/2016 |
| WO | WO 2020/243425 | 12/2020 |

OTHER PUBLICATIONS

Official Action for U.S. Appl. No. 17/591,951, dated Nov. 16, 2023 72 pages.
Notice of Allowance for U.S. Appl. No. 17/591,904, dated Jan. 10, 2024 8 pages.
Kim et al. "Feasibility Study of Precise Balloon Catheter Tracking and Visualization with Fast Photoacoustic Microscopy," Sensors, Oct. 2020, vol. 20, No. 19, pp. 5585.
Srivastava et al. "Unsupervised Deep Learning based Longitudinal Follicular Growth Tracking during IVF Cycle using 3D Transvaginal Ultrasound in Assisted Reproduction," IEEE, 2021 43rd Annual International Conference of the IEEE Engineering in Medicine & Biology Society (EMBC), Nov. 2021, pp. 3209-3212.
Yeung et al. "ImplicitVol: Sensorless 3D Ultrasound Reconstruction with Deep Implicit Representation," arxiv.org, Sep. 24, 2021, 11 pages.
Invitation to Pay Additional Fees for International (PCT) Patent Application No. PCT/IB2023/050792, dated Apr. 6, 2023, 15 pages.
International Search Report and Written Opinion for International (PCT) Patent Application No. PCT/IB2023/050792, dated May 30, 2023, 21 pages.
International Search Report and Written Opinion for International (PCT) Patent Application No. PCT/IB2023/050646, dated May 15, 2023, 10 pages.
International Search and Written Opinion for International (PCT) Patent Application No. PCT/IB2023/050675, dated Apr. 26, 2023, 11 pages.
International Search Report and Written Opinion for International (PCT) Patent Application No. PCT/IB2023/050678, dated Apr. 24, 2023, 14 pages.
U.S. Appl. No. 17/591,904, filed Feb. 3, 2022.
U.S. Appl. No. 17/591,919, filed Feb. 3, 2022.
U.S. Appl. No. 17/591,951, filed Feb. 3, 2022.
U.S. Appl. No. 17/591,974, filed Feb. 3, 2022.
Official Action for U.S. Appl. No. 17/591,951, dated Mar. 27, 2024 74 pages.
Official Action for U.S. Appl. No. 17/591,951, dated Aug. 29, 2024 15 pages.

* cited by examiner

SYSTEMS, METHODS, AND DEVICES FOR RECONSTRUCTING A THREE-DIMENSIONAL REPRESENTATION

FIELD

The present technology generally relates to imaging and image processing, and relates more particularly to generating a three-dimensional representation of, for example, one or more anatomical elements capable of use for navigation.

BACKGROUND

Imaging devices may be used by a medical provider for diagnostic and/or therapeutic purposes. Images may be obtained from imaging devices using different modalities at various times (e.g., preoperatively, intraoperatively, postoperatively). Such images may also contain various information (e.g., soft tissue and/or hard tissue) based on the nature of the imaging device used to capture the images.

SUMMARY

Example aspects of the present disclosure include:

A system for reconstructing a three-dimensional representation according to at least one embodiment of the present disclosure comprises an imaging device; a processor; and a memory storing data for processing by the processor, the data, when processed, causing the processor to: orient the imaging device at one or more poses; receive an image at each of the one or more poses to form a set of images, the set of images depicting one or more anatomical elements; receive pose information at each of the one or more poses; input the set of images and the pose information to a reconstruction model, the reconstruction model configured to generate a three-dimensional representation of the one or more anatomical elements based on the set of images and the pose information; and receive, from the reconstruction model, the three-dimensional representation of the one or more anatomical elements.

Any of the aspects herein, wherein the set of images comprise one or more two-dimensional images.

Any of the aspects herein, further comprising a navigation system configured to track at least the imaging device, wherein the pose information is received from the navigation system.

Any of the aspects herein, wherein the imaging device is an ultrasound imaging device.

Any of the aspects herein, wherein the memory stores further data for processing by the processor that, when processed, causes the processor to: generate instructions for navigating at least one instrument based on the three-dimensional representation.

Any of the aspects herein, wherein the memory stores further data for processing by the processor that, when processed, causes the processor to: segment at least one of the one or more anatomical elements from the three-dimensional representation.

Any of the aspects herein, wherein the memory stores further data for processing by the processor that, when processed, causes the processor to: receive at least one updated image; receive updated pose information corresponding to the at least one updated image; input the at least one updated image and the pose information to the reconstruction model, the reconstruction model configured to generate an updated three-dimensional representation of the one or more anatomical elements based on the at least one updated image and the updated pose information; and receive, from the reconstruction model, an updated three-dimensional representation of the one or more anatomical elements.

Any of the aspects herein, wherein generating the updated three-dimensional representation comprises replacing at least one of the one or more images with the at least one updated image.

Any of the aspects herein, wherein the at least one updated image is obtained for at least one of the one or more poses.

Any of the aspects herein, wherein the at least one updated image is obtained at one or more updated poses.

Any of the aspects herein, wherein the memory stores further data for processing by the processor that, when processed, causes the processor to receive a preoperative image and preoperative pose information, wherein inputting the set of images and the pose information into the reconstruction model includes inputting the preoperative image and the preoperative pose information into the reconstruction model, and wherein generating the three-dimensional representation is additionally based on the preoperative image.

Any of the aspects herein, wherein the reconstruction model is training using at least one of historical sets of images, historical pose information, and historical preoperative images.

Any of the aspects herein, wherein the imaging device is oriented by at least one robotic arm, and wherein the pose information is obtained from the at least one robotic arm.

A device for reconstructing a three-dimensional representation according to at least one embodiment of the present disclosure comprises a processor; and a memory storing data for processing by the processor, the data, when processed, causing the processor to: orient the imaging device at one or more poses; receive an image at each of the one or more poses to form a set of images, the set of images depicting one or more anatomical elements; receive pose information at each of the one or more poses; input the set of images and the pose information to a reconstruction model, the reconstruction model configured to generate a three-dimensional representation of the one or more anatomical elements based on the set of images and the pose information; and receive, from the reconstruction model, the three-dimensional representation of the one or more anatomical elements.

Any of the aspects herein, wherein the memory stores further data for processing by the processor that, when processed, causes the processor to: segment at least one of the one or more anatomical elements from the three-dimensional representation.

Any of the aspects herein, wherein the memory stores further data for processing by the processor that, when processed, causes the processor to: receive at least one updated image; receive updated pose information corresponding to the at least one updated image; input the at least one updated image and the pose information to the reconstruction model, the reconstruction model configured to generate an updated three-dimensional representation of the one or more anatomical elements based on the at least one updated image and the updated pose information; and receive, from the reconstruction model, an updated three-dimensional representation of the one or more anatomical elements based on the at least one updated image and the updated pose information.

Any of the aspects herein, wherein generating the updated three-dimensional representation comprises replacing at least one of the one or more images with the at least one updated image.

Any of the aspects herein, wherein the at least one updated image is obtained for at least one of the one or more poses.

Any of the aspects herein, wherein the at least one updated image is obtained for at one or more updated poses.

A system for reconstructing an image according to at least one embodiment of the present disclosure comprises an imaging device; a navigation system; a processor; and a memory storing data for processing by the processor, the data, when processed, causing the processor to: orient the imaging device at one or more poses; receive an image at each of the one or more poses to form a set of images, the set of images depicting one or more anatomical elements; receive pose information at each of the one or more poses from the navigation device; input the set of images and the pose information to a reconstruction model, the reconstruction model configured to generate a three-dimensional representation of the one or more anatomical elements based on the set of images and the pose information; and receive, from the reconstruction model, the three-dimensional representation of the one or more anatomical elements.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided herein below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions or algorithms may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Navigation systems may be used to provide navigation for a surgeon or a robotic system during a surgical procedure. Such systems may provide navigation relative to, for example, a preoperative image (e.g., a magnetic resonance image (MRI) or computed tomography (CT) image) depicting one or more anatomical elements. However, during a surgical procedure, if the one or more anatomical elements move or shift, then the navigation system may no longer be accurate and may require updating.

According to at least one embodiment of the present disclosure, ultrasound imaging can be used with the navigation system to provide updated imaging of the one or more anatomical elements, which can provide updated information about a pose of the one or more anatomical elements. The pose includes a position and an orientation. The updated images may also be aligned with the preoperative image. Thus, integration of ultrasound and navigation can provide real-time updated imaging of one or more anatomical elements to ensure that the navigation system is navigating relative to a current pose of the one or more anatomical elements.

There are also a number of advantages that combining ultrasound imaging with surgical navigation can offer. Ultrasound does not emit harmful radiation and thus, can be used continuously during a surgical procedure without exposing a patient and a surgical team to radiation. This results in a safer environment for the patient, surgeon, and surgical team. Ultrasound may also be helpful to track certain objects and/or anatomical elements (e.g., soft tissue) as compared to, for example, X-ray based imaging, which may be better suited for other objects/anatomical elements (e.g., hard tissue, manmade objects, etc.). Ultrasound with navigation can be used for multiple applications such as, for example, cranial and/or spinal procedures. Current imaging and navigation can overlay an ultrasound image over a pre-operative image (e.g., an MRI or CT image); take measurements on ultrasound images; and/or capture a series of images and play through the images.

In at least one embodiment, ultrasound navigation may be used for, for example, three-dimensional ultrasound navigation; electromagnetic navigated ultrasound; augment reality; using artificial intelligence to merge ultrasound with pre-operative imaging for real-time brain shift compensation; reconstructing patient anatomy of interest (e.g., vascular and/or tumor); patient auto-registration; tumor ablation confirmation; tracking hardening of biologics; track size of tool (e.g., a balloon) between anatomical elements (e.g., vertebrae); and/or segmental tracking.

Embodiments of the present disclosure provide technical solutions to one or more of the problems of (1) providing a three-dimensional representation of one or more anatomical elements; (2) updating a three-dimensional representation of one or more anatomical elements during a surgical procedure; (3) providing real-time updates of a pose, size, or shape of one or more anatomical elements to a navigation system; (4) providing navigation using three-dimensional representation of one or more anatomical elements; and (5) increasing patient safety.

Figure 1:
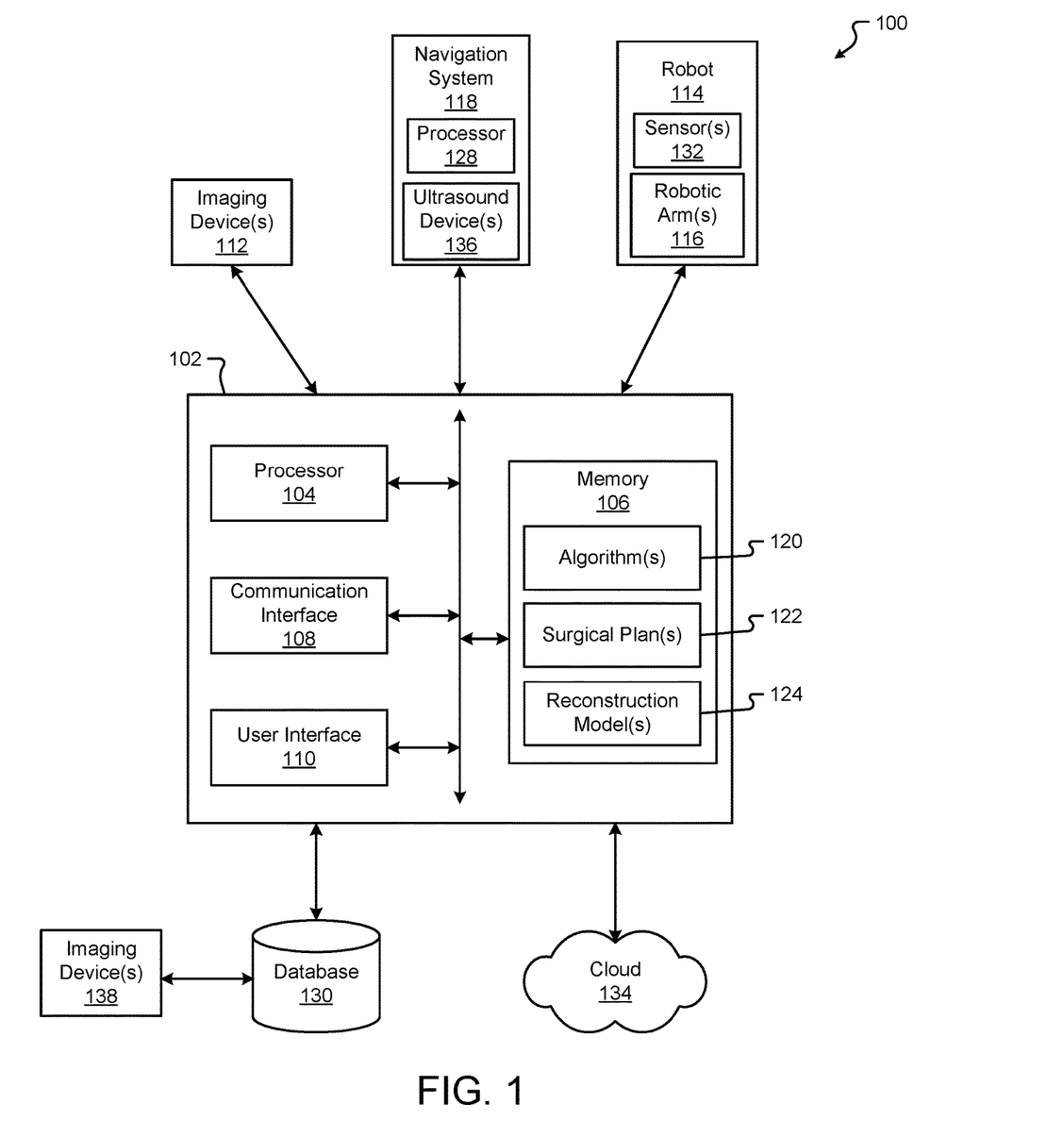
FIG. 1 is a block diagram of a system according to at least one embodiment of the present disclosure.

Turning first to FIG. 1, a block diagram of a system 100 according to at least one embodiment of the present disclosure is shown. The system 100 may be used to generate a three-dimensional representation or multiple three-dimensional representations of one or more anatomical elements, which may be used for robot navigation during a surgical procedure, and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300, 400, 500 described herein, or of any other methods. The memory 106 may store, for example, one or more algorithms 120, one or more surgical plans 122, and/or one or more reconstruction models 124. Such algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as algorithms, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134. The reconstruction models 124 may be trained (as described with respect to FIG. 2), then made available to the computer device 102 to enable generating three-dimensional representations of one or more objects, anatomical elements, tools, and/or instruments.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. The imaging device 112 may be capable of capturing a two-dimensional image, a series of two-dimensional images, a three-dimensional image, and/or a series of three-dimensional images to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient.

In some embodiments, the imaging device 112 may comprise more than one imaging device 112. For example, a first imaging device may provide first image data and/or a first image at a first time, and a second imaging device may provide second image data and/or a second image at the first time or at a second time after the first time. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 112 may comprise a source and a detector. In such embodiments, the imaging device 112 may be an ultrasound device or an x-ray imaging device. In some embodiments, the source and the detector may be in separate housings or are otherwise physically separated. In such embodiments, the source may be oriented by a first robotic arm and the detector may be oriented by a second robotic arm, as will be described in more detail below. In other embodiments, the source and the detector may be in the same housing. The source may be configured to emit a wave and the detector may be configured to receive a signal indicative of the emitted wave. The detector may also be configured to save a plurality of image datasets to, for example, the memory 106.

In some embodiments, the imaging device 112 may be a first imaging device 112 and the system 100 may include a second imaging device 138, which may be the same as or similar to the imaging device 112. The second imaging device 138 may be in communication with the database 130. The second imaging device 138 may provide preoperative images, which may be stored in the database 130 for use at a later time. For example, a preoperative image of a patient may be obtained at a date prior to a surgical procedure. The preoperative image may be stored in the database 130 (whether as part of the surgical plan 122 or separately) and retrieved anytime thereafter. In other instances, the second imaging device 138 may provide a preoperative image prior to a start of a surgical procedure. The second imaging device 138 in some embodiments may use a different modality than the first imaging device 112. For example, the second imaging device 138 may be a CT or MRI scanner and the first imaging device 112 may be an ultrasound device.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure.

The robot 114 may comprise one or more robotic arms 116. The robotic arms may be controlled in a single, shared coordinate space, or in separate coordinate spaces. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components such as, for example, the source and the detector, one robotic arm 116 may hold the source, and another robotic arm 116 may hold the detector. Each robotic arm 116 may be accurately positionable independently of the other robotic arm (e.g., the detector can be positioned or oriented independently of the source). In some embodiments, one robotic arm 116 may orient the source at a first pose across from the detector oriented by another robotic arm 116 at a second pose. In some embodiments, the source may remain at the same pose while the detector is oriented at different poses. In other embodiments, the detector may remain at the same pose while the source is oriented at different poses. In still other embodiments, both the detector and the source may each be oriented at different poses.

The robot 114, together with the robotic arm 116, may have, for example, one, two, three, four, five, six, seven, or more degrees of freedom. Further, the robotic arm 116 may be positioned or positionable in any pose, plane, and/or focal point. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm). Each sensor 132 may be any kind of sensor 132 for measuring the pose in space of the robotic arm 116. The sensor 132 may comprise one or more or any combination of components that are electrical, mechanical, electro-mechanical, magnetic, electromagnetic, or the like. The sensor 132 may comprise, but is not limited to, one or more of a linear encoder, a rotary encoder, a capacitor, and/or an accelerometer. In some embodiments, the sensor 132 may include a memory for storing sensor data. In still other examples, the sensor 132 may output signals (e.g., sensor data) to one or more sources (e.g., the computing device 102, the navigation system 118, and/or the robot 114).

The sensor 132 may be integrated internally into the robotic arm 116 or otherwise positioned inside of the robotic arm. In some embodiments, the sensor 132 is positioned inside a joint of the robotic arm 116. The sensor 132 may include a plurality of sensors and each sensor may be positioned at the same location or a different location as any other sensor. For example, a sensor 132 may be positioned in one or more joints of the robotic arm 116. It will be appreciated that in some embodiments the sensor 132 can be positioned at or on any component of the system 100 or environment (e.g., on any portion of the navigation system 118, the robot 114, the robotic arm 116, and/or any other component at the surgical site).

The sensor 132 may be operable to sense and/or monitor the pose (e.g., position and orientation), position, or orientation of any portion of the robotic arm 116. The sensor 132 may send the data to the computing device 102 at any time, whether continuously, at a time interval, in response to an input from a user requesting the data, or a change in pose, position, or orientation of the robotic arm 116. Further, in some embodiments, the sensor 132 may send data to the computing device 102 to display on the user interface 110.

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

In some embodiments, electromagnetic sensor(s) may be used to track any component of the system 100 including, for example, the imaging device 112. The electromagnetic sensor(s) may be used by the navigation system 118 to track a corresponding component. For example, an electromagnetic sensor may be disposed on or integrated with an ultrasound transducer for tracking a pose of the transducer in real-time. In some embodiments, the electromagnetic sensor may be removable.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker or an electromagnetic sensor attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In some embodiments, an ultrasound device 136 may be integrated with the navigation system 118 in which images from the ultrasound device may be used by the navigation system 118 for navigation. In some embodiments, the hardware for an ultrasound device 136 may be directly integrated with the navigation system 118 hardware. In other embodiments, the ultrasound device 136 may be a separate component. Whether directly integrated or combined as separate components, a processor such as the processor 104 or a processor 128 of the navigation system 118 may receive data from the ultrasound device 136 and automatically process such data for use by the navigation system 118.

In embodiments using an integrated navigation system 118 and ultrasound device 136, the navigation system 118 may navigate a surgeon or robotic system relative to a preoperative image (e.g., MRI or CT image(s)) depicting one or more anatomical elements, and an ultrasound probe may provide real-time or live imaging of the one or more anatomical elements during a surgical procedure. The preoperative image(s) may be obtained from, for example, the database 130 and/or the second imaging device 138. The real-time or live image(s) obtained from the ultrasound device 136 can be aligned with preoperative image(s) (e.g., MRI or CT images) to confirm or—in instances where an anatomical element has moved—update a pose of the anatomical element and surrounding anatomical elements. The navigation system 118 may then provide navigation based on the updated pose of the anatomical element(s). Thus, the ultrasound device 136 enables the navigation system 118 to continue to navigate when one or more anatomical elements shift or move, either in space or relative to one another. In some instances, the real-time or live image(s) can be used to generate a three-dimensional ultrasound representation that can be overlaid onto a preoperative three-dimensional representation generated from preoperative image(s). The navigation system 118 may then navigate based on the three-dimensional ultrasound representation. In some instances, the real-time or live image(s) can be used to generate a three-dimensional ultrasound representation that can be overlaid onto a preoperative two-dimensional image that depicts the anatomical elements.

The combined navigation system 118 and ultrasound device 136 may be used in various applications. For example, the combined navigation system 118 and ultrasound device 136 may be used to view a progress of or confirm a tumor ablation, while the tumor is in the process of being ablated. In such examples, a navigated ultrasound probe may be used to obtain a current ultrasound image of an ablated tumor area, which may be compared to a preoperative image obtained prior to the ablation procedure. In another example, the combined navigation system 118 and ultrasound device 136 may be used to auto-register and/or reregister a patient. In such examples, images obtained from the ultrasound device 136 may be automatically aligned and correlated to preoperative images. In still another example, the combined navigation system 118 and ultrasound device 136 may be used generate a three-dimensional representation of one or more anatomical elements based on a set of images and corresponding pose information that can be used by the navigation system 118 for navigation, as will be described in detail in FIGS. 3-5.

The database 130 may store, for example, the one or more algorithms 120, the one or more surgical plans 122 (including, for example, preoperative image(s); steps for orienting the imaging device 112 at one or more poses; etc.); one or more images useful in connection with a surgery to be completed by or with the assistance of one or more other components of the system 100 (e.g., preoperative images from the second imaging device 138); and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the model architecture 200 and/or methods 300, 400, 500 described herein. The system 100 or similar systems may also be used for other purposes.

Figure 2:
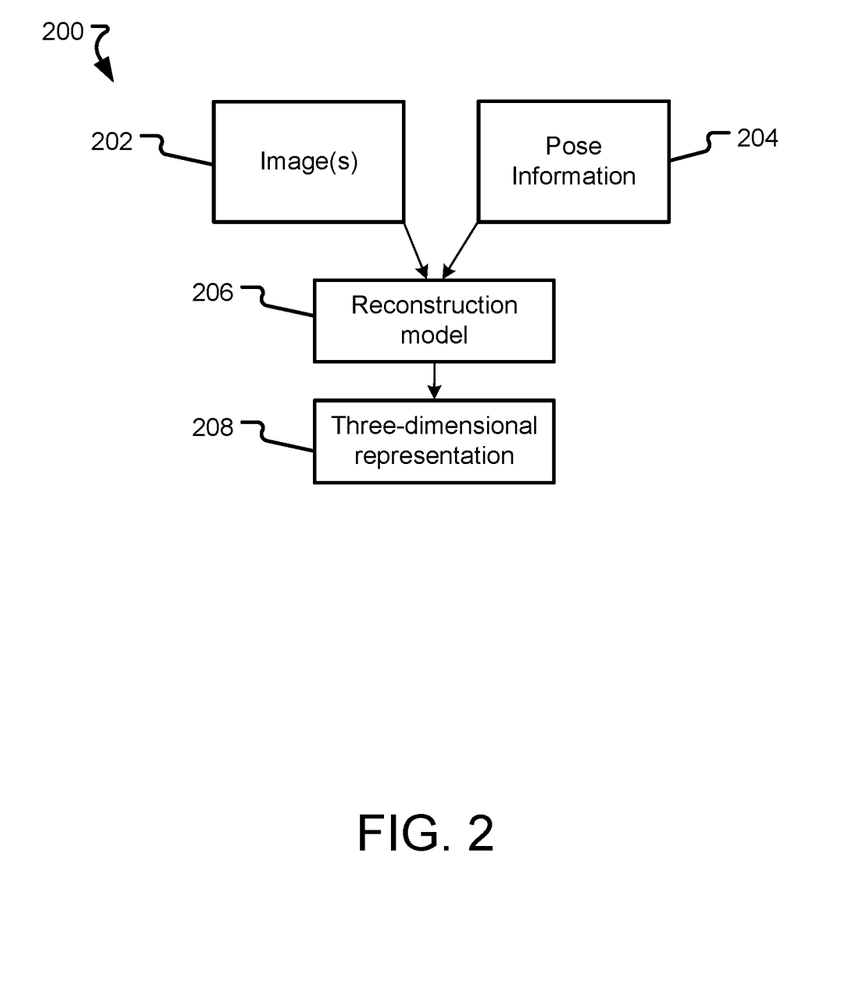
FIG. 2 is a flowchart according to at least one embodiment of the present disclosure.

Turning to FIG. 2, an example of a model architecture 200 that supports methods and systems (e.g., Artificial Intelligence (AI)-based methods and/or system) for generating a three-dimensional representation of one or more anatomical elements is shown. It will be appreciated that a three-dimensional representation may be generated for one or more objects, instruments, and/or tools.

A set of images 202 may be obtained by an imaging device such as the imaging device 112. In some embodiments the imaging device may be an ultrasound device. The set of images 202 may depict one or more objects and/or one or more anatomical elements of, for example, a patient. The set of images 202 may be obtained at any time such as, for example, preoperatively, intraoperatively, or postoperatively.

Pose information 204 corresponding to the set of images 202 may be obtained. The pose information 204 may be, for example, separate from the set of images and may comprise coordinates of the imaging device when a corresponding image is obtained. The pose information 204 may be useful for determining a spatial relationship between the set of images 202. In some embodiments, the pose information 204 may be obtained from a navigation system such as the navigation system 118 which may be configured to track the imaging device 112. The imaging device 112 may be tracked using, for example, reference markers or electromagnetic trackers. In other embodiments, the imaging device 112 may be supported by a robotic arm such as the robotic arm 116 and pose information may be obtained from sensors such as the sensors 132 integrated with or disposed on the robotic arm 116. The sensors 132 may be configured to track, among other things, a pose of the robotic arm 116. More specifically, a pose of an end of the robotic arm 116 may be tracked, or may be determined from a pose of any portion of the robotic arm 116. The pose of the robotic arm 116 may correlate to a pose of the imaging device 112 when the imaging device 112 is oriented by the robotic arm 116.

The set of images 202 and the pose information 204 are received as input by the reconstruction model 206, 124 which may be the same as or similar to the reconstructions model 124 stored in the memory 106. The reconstruction model 206 may be trained using historical image(s) and/or historical pose information. In other embodiments, the reconstruction model 206 may be trained using the set of images 202 and/or the pose information 204. In such embodiments, the reconstruction model 206 may be trained prior to inputting the images 202 and the pose information 204 into the reconstruction model 206 or may be trained in parallel with inputting the set of images 202 and the pose information 204. Training in parallel may, in some embodiments, comprise training a reconstruction model 206 using the set of images 202 and the pose information 204 while also using a separate reconstruction model 206 to generate the three-dimensional representation 208 using the set of images 202 and the pose information 204. In some instances, when the reconstruction model 206 being trained exceeds the reconstruction model 206 in use (whether in efficiency, accuracy, or otherwise), the reconstruction model 206 being trained may replace the reconstruction model 206 in use. Such parallel training may be useful, for example, in situations, where the reconstruction model 206 is continuously in use (for example, when the at least one image is continuously updated) and a corresponding reconstruction model 206 may be trained in parallel for further improvements.

The reconstruction model 206 may be configured to generate a three-dimensional representation 208 of the one or more anatomical elements. Generating the three-dimensional representation 208 may include determining a surface representation or virtual boundary of the one or more anatomical elements depicted in the set of images 202 based on the corresponding pose information. More specifically, in some embodiments, each image may be positioned adjacent to another image based on the respective corresponding pose information and a surface representation may be formed based the relative position of surfaces depicted in each image. In some embodiments, the surface representation may be a virtual mesh. The virtual mesh may comprise, for example, a set of polygonal faces that, when taken together, form a surface covering of a virtual object. The set of polygonal faces may be connected at their edges and vertices to define a shape of the virtual object.

Figure 3:
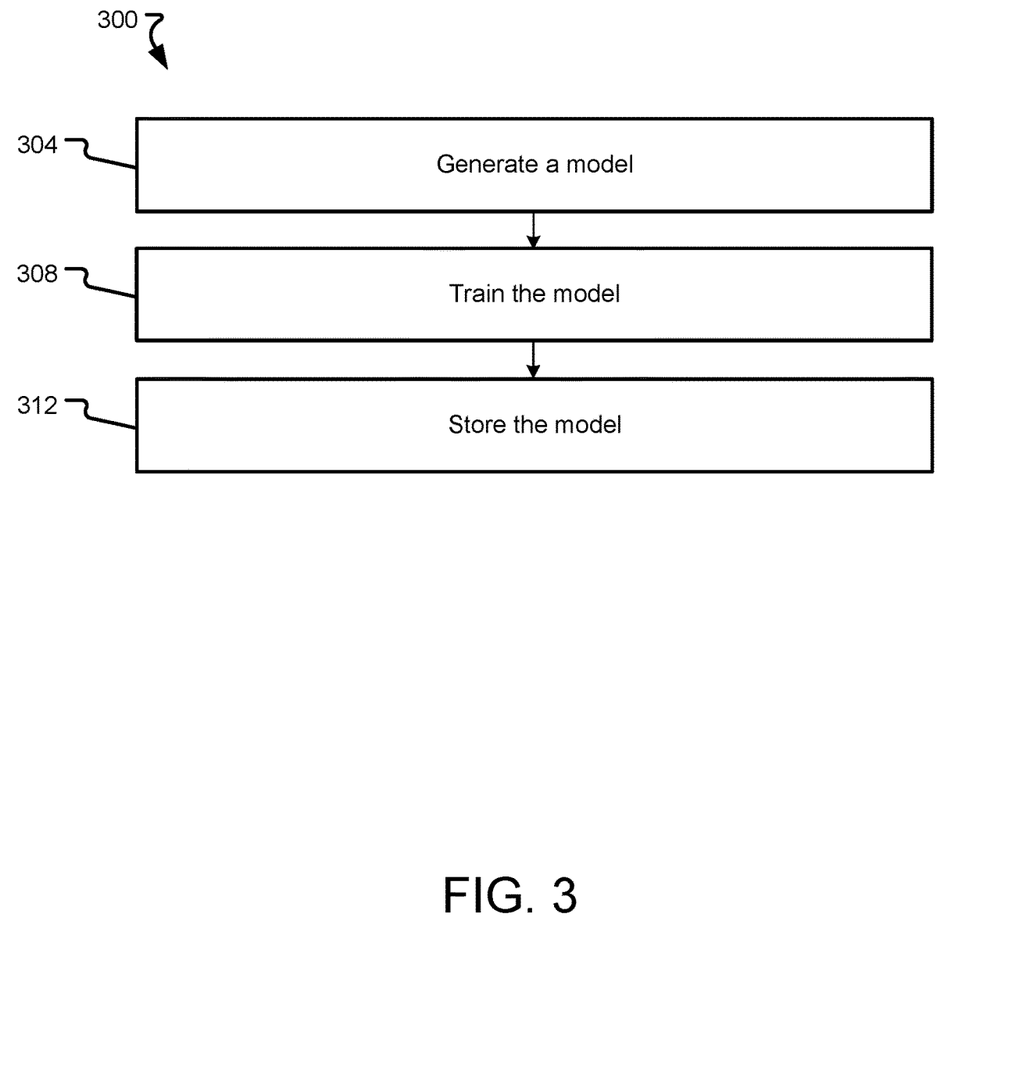
FIG. 3 is a flowchart according to at least one embodiment of the present disclosure.

Turning to FIG. 3, a method 300 that may be used, for example, for generating a model is provided.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 210. The at least one processor may perform the method 210 by executing instructions stored in a memory such as the memory 106. The instructions may correspond to one or more steps of the method 210 described below. The instructions may cause the processor to execute one or more algorithms, such as the algorithm 120.

The method 300 comprises generating a model (step 304). The model may be the reconstruction model 206, 124. A processor such as the processor 104, 128 may generate the model. The model may be generated to facilitate and enable, for example, generating of a three-dimensional representation of one or more anatomical elements and/or objects.

The method 300 also comprises training the model (step 308). In embodiments where the model is trained prior to a surgical procedure, the model may be trained using historical data from a number of patients. In some embodiments, the historical data may be obtained from patients that have similar patient data to a patient on which a surgical procedure is to be performed. In other embodiments, the historical data may be obtained from any patient.

In other embodiments, the model may be trained in parallel with use of another model. Training in parallel may, in some embodiments, comprise training a model using input received during, for example, or prior to a surgical procedure, while also using a separate model to receive and act upon the same input. Such input may be specific to a patient undergoing the surgical procedure. In some instances, when the model being trained exceeds the model in use (whether in efficiency, accuracy, or otherwise), the model being trained may replace the model in use. Such parallel training may be useful, for example, in situations, where a model is continuously in use (for example, when an input (such as, for example, an image) is continuously updated) and a corresponding model may be trained in parallel for further improvements.

In some embodiments, it will be appreciated that the model trained using historical data may be initially used as a primary model at a start of a surgical procedure. A training model may also be trained in parallel with the primary model using patient-specific input until the training model is sufficiently trained. The primary model may then be replaced by the training model.

The method 300 also comprises storing the model (step 312). The model may be stored in memory such as the memory 106 for later use. In some embodiments, the model is stored in the memory when the model is sufficiently trained. The model may be sufficiently trained when the model produces an output that meets a predetermined threshold, which may be determined by, for example, a user, or may be automatically determined by a processor such as the processor 104, 128.

The present disclosure encompasses embodiments of the method 300 that comprise more or fewer steps than those described above, and/or one or more steps that are different than the steps described above.

Figure 4:
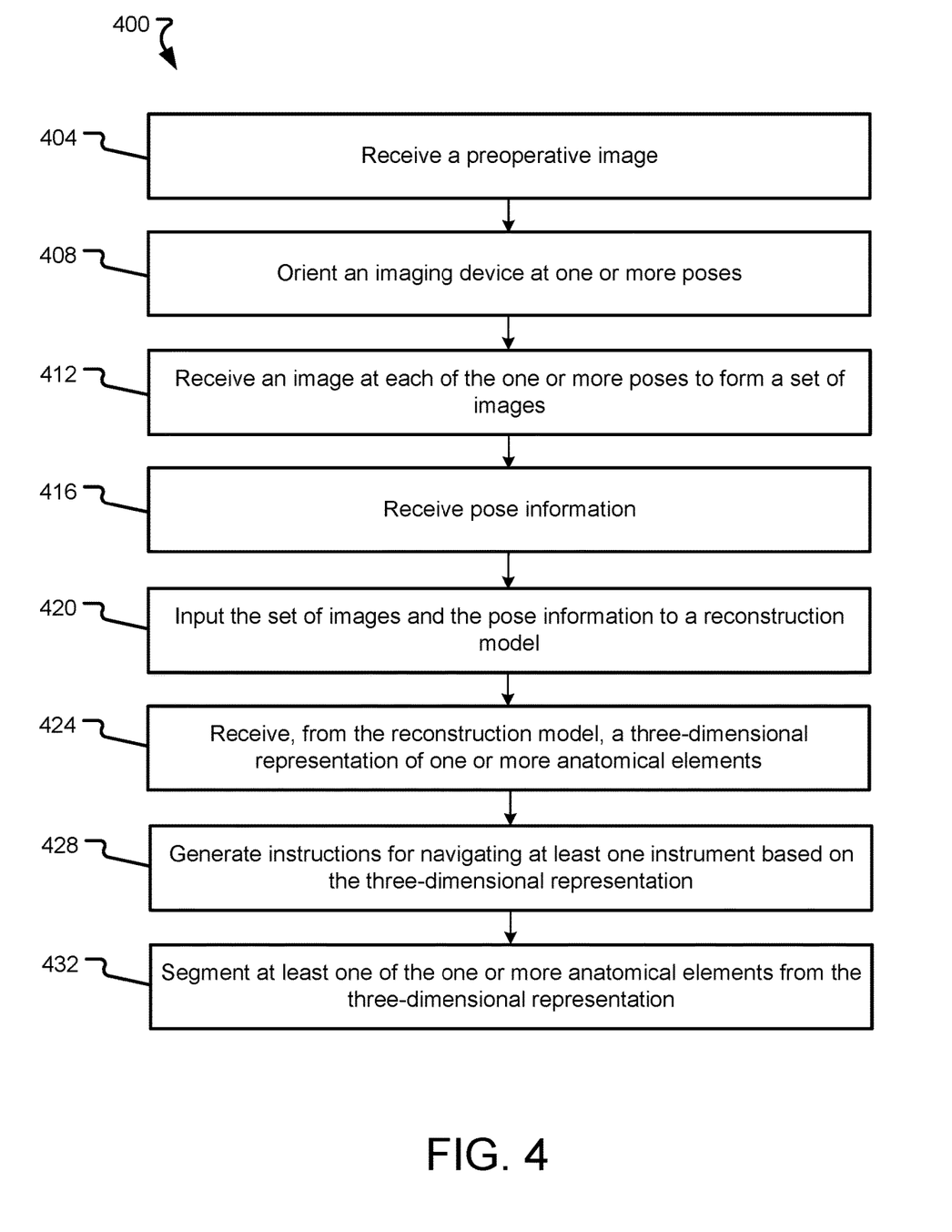
FIG. 4 is a flowchart according to at least one embodiment of the present disclosure.

FIG. 4 depicts a method 400 that may be used, for example, for generating a three-dimensional representation of one or more anatomical elements.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as the algorithm 120.

The method 400 comprises receiving a preoperative image (step 404). The preoperative image may be obtained from an imaging device such as the second imaging device 138 and/or a database such as the database 130. In some embodiments, the second imaging device is a CT scanner or an MRI scanner. The preoperative image may comprise one or more two-dimensional images, one or more three-dimensional images, or a combination of one or more two-dimensional images and one or more three-dimensional images. In some embodiments, the preoperative image may be obtained from a surgical plan such as the surgical plan 122. In other embodiments, the preoperative image may be received via a user interface such as the user interface 110 and/or via a communication interface such as the communication interface 108 of a computing device such as the computing device 102, and may be stored in a memory such as the memory 106. The image data may also be generated by and/or uploaded to any other component of the system 100. In some embodiments, the preoperative image may be indirectly received via any other component of the system 100 or a node of a network to which the system 100 is connected.

The preoperative image may depict one or more anatomical elements. In some embodiments, the preoperative image may contain hard tissue information about the one or more anatomical elements. In other embodiments, the preoperative image may contain soft tissue information about the one or more anatomical elements.

The method 400 also comprises orienting an imaging device at one or more poses (step 408). The imaging device may be the same as or similar to the imaging device 112 or an ultrasound device such as the ultrasound device 136. In some embodiments, the ultrasound device is integrated with a navigation system such as the navigation system 118. In some embodiments, the imaging device may be oriented by a robotic arm such as the robotic arm 116 at the one or more poses. In other embodiments, the imaging device may be oriented by a user at the one or more poses.

The one or more poses may be obtained from, for example, a surgical plan such as the surgical plan 122. In other embodiments, the one or more poses may be received via a user interface such as the user interface 110 and/or via a communication interface such as the communication interface 108 of a computing device such as the computing device 102, and may be stored in a memory such as the memory 106. In still other embodiments, the one or more poses may be automatically determined by a processor such as the processor 104, 128. In such embodiments, a user such as a surgeon or other medical provider may select one or more anatomical elements to image and the processor may determine the one or more poses to obtain images of the one or more anatomical elements.

The method 400 also comprises receiving an image at each of the one or more poses to form a set of images (step 412). The set of images may be the same as or similar to the set of images 202. Each image of the set of images may be, in some instances, a two-dimensional image. The set of images may depict one or more anatomical elements. The one or more anatomical elements depicted in the set of images may be the same as the one or more anatomical elements depicted in the preoperative image. In other instances, the set of images may depict at least one of the one or more anatomical elements depicted in the preoperative image.

It will be appreciated that each image of the set of images may depict the one or more anatomical elements from different angles or viewpoints as defined by each pose of the one or more poses. In some instances, some of the images of the set of images may depict one anatomical element and other images of the set of images may depict another anatomical element. In other instances, the set of images may depict the same anatomical element(s).

The method 400 also comprises receiving pose information (step 416). The pose information may be pose information for each pose of the one or more poses (which correspond to each image of the set of images). As previously described, the pose refers to a position and an orientation. The pose information may be, for example, coordinates of the imaging device when a corresponding image is obtained. In some embodiments, the pose information may be obtained from a navigation system such as the navigation system 118. In such embodiments, the imaging device may include a reference marker or an electromagnetic tracker tracked by the navigation system. In other embodiments, the pose information may be obtained from a robotic arm such as the robotic arm 116 when the imaging device is oriented by the robotic arm. In such embodiments, the robotic arm may comprise a sensor such as the sensor 142 configured to provide pose data of the robotic arm. The sensor may provide pose data of an end of the robotic arm (e.g., a pose of the imaging device disposed at the end of the robotic arm) or may provide pose data of any portion of the robotic arm. In the latter instances, a pose of the imaging device can be determined from the pose data based on a distance between the portion of the robotic arm and the imaging device.

It will be appreciated that in some embodiments, the pose information may only contain information about a position or an orientation of the imaging device.

The method 400 also comprises inputting the set of images and the pose information to a reconstruction model (step 420). The reconstruction model may be the same as or similar to the reconstruction model 206, 124. The reconstruction model may be configured to generate a three-dimensional representation of the one or more anatomical elements based on the set of images and the pose information. In some embodiments, the preoperative image and corresponding preoperative pose information may also be inputted into the reconstruction model. In at least some embodiments, the reconstruction model may generate the three-dimensional representation of the one or more anatomical elements based on the set of images, the pose information, the preoperative image, and the preoperative pose information. In other instances, the reconstruction model may output a separate three-dimensional representation of one or more anatomical elements depicted in the preoperative image. In such instances, the three-dimensional representation of the one or more anatomical elements depicted in the set of images may be overlaid or compared to the three-dimensional representation of the one or more anatomical elements depicted in the preoperative image. For example, the three-dimensional representation of the one or more anatomical elements depicted in the set of images may be formed from ultrasound images, which may be overlaid onto the three-dimensional representation of the one or more anatomical elements depicted in the preoperative image, which may be formed from X-ray images. Thus, in such examples, soft tissue information (as obtained from the ultrasound images) and hard tissue information (as obtained from the X-ray images) may both be provided for the one or more anatomical elements.

The reconstruction model may be trained using historical sets of image(s) and/or historical pose information. In some embodiments, the historical sets of image(s) may depict one or more anatomical elements similar to the one or more anatomical elements depicted by the preoperative image. In other embodiments, the historical sets of image(s) may depict one or more anatomical elements different from the one or more anatomical elements depicted by the preoperative image.

Generating the three-dimensional representation may include determining a surface representation or virtual boundary of the one or more anatomical elements depicted in the set of images (and, in some cases, the preoperative image) based on the corresponding pose information (and, in some cases, the preoperative pose information). More specifically, in some embodiments, each image may be positioned adjacent to another image based on the respective corresponding pose information and a surface representation may be formed based the relative position of surfaces depicted in each image.

The method 400 also comprises receiving, from the reconstruction model, a three-dimensional representation of one or more anatomical elements (step 424). As described above, the three-dimensional representation of the one or more anatomical elements may comprise a surface representation of the one or more anatomical elements. In some embodiments, the surface representation may be a virtual mesh. The three-dimensional representation may also comprise pose information of the one or more anatomical elements. In some embodiments, the three-dimensional representation may comprise hard tissue and/or soft tissue information. Further, the three-dimensional representation may be measured to provide information about a size, volume, dimensions, or shape of the one or more anatomical elements.

The method 400 also comprises generating instructions for navigating based on the three-dimensional representation of the one or more anatomical elements (step 428). A navigation system such as the navigation system 118 may provide the navigation. The instructions may be generated for navigating one or more instruments, tools, and/or anatomical elements, by a user such as a surgeon or other medical provide or by a robotic arm such as the robotic arm 116. The instructions may be generated by a processor such as the processor 104, 128 (whether of the navigation system or as a separate component). The instructions may be machine readable data and transmitted to, for example, the robotic arm to cause the robotic arm to execute the instructions. The instructions may also be human readable data and may be displayed on a user interface such as the user interface 110 for instructing the user.

The method 400 also comprises segmenting at least one of the one or more anatomical elements from the three-dimensional representation (step 442). Segmenting at least one of the one or more anatomical elements from the three-dimensional representation of the one or more anatomical elements may comprise identifying a boundary of the at least one anatomical element and forming a separate three-dimensional representation of the at least one anatomical element. In some embodiments, identifying the boundary may comprise identifying adjacent sets of pixels having a large enough contrast to represent a border of an anatomical element depicted therein. In other embodiments, feature recognition may be used to identify a border of an anatomical element. For example, a contour of a vertebrae may be identified using feature recognition. The three-dimensional representation of the at least one anatomical element may be separately tracked and/or updated.

The present disclosure encompasses embodiments of the method 400 that comprise more or fewer steps than those described above, and/or one or more steps that are different than the steps described above.

Figure 5:
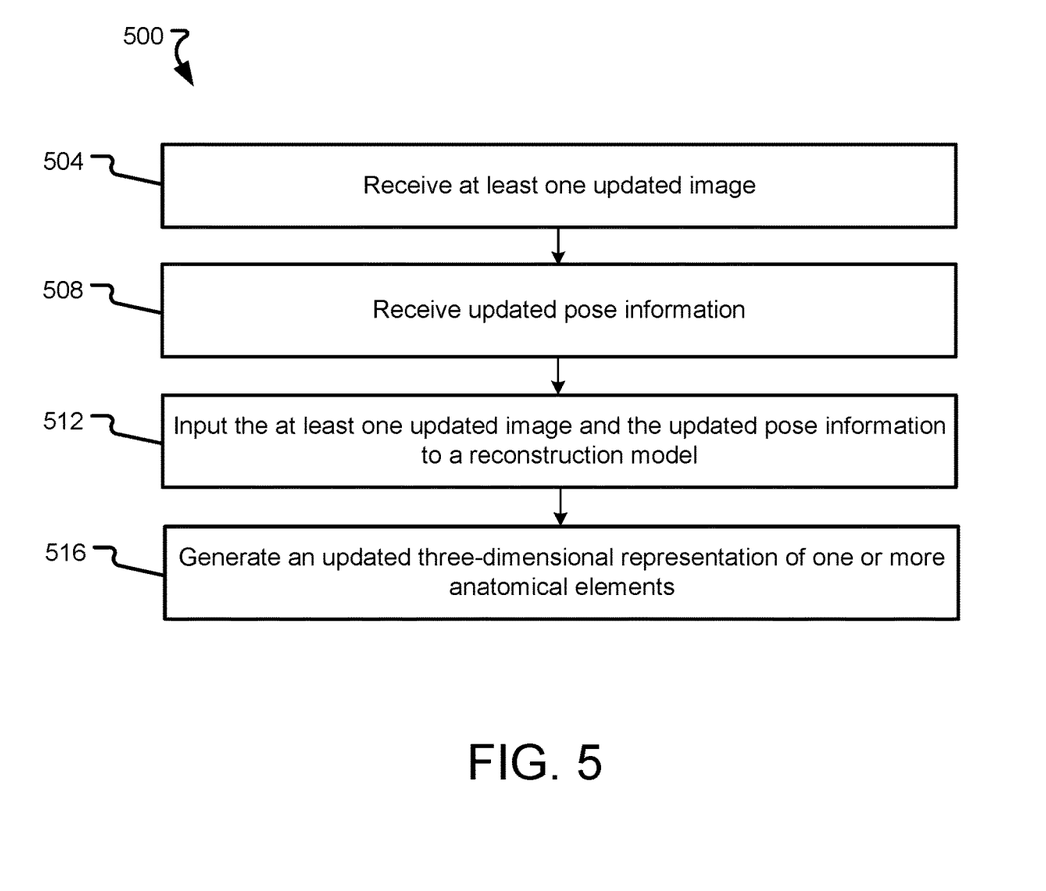
FIG. 5 is a flowchart according to at least one embodiment of the present disclosure.

FIG. 5 depicts a method 500 that may be used, for example, for generating an updated three-dimensional representation of one or more anatomical elements.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as the algorithm 120.

The method 500 comprises receiving at least one updated image (step 504). The step 504 may be the same or similar to the step 408 of method 400 described above. The at least one updated image may be received from the same imaging device as the set of images. In other instances, the at least one updated image may be received from a different imaging device as the set of images. The at least one updated image may depict one or more anatomical elements, which may be the same as or similar to the one or more anatomical elements depicted in the set of images. In some embodiments, the at least one updated image may be obtained from at least one of the one or more poses. In other embodiments, the at least one updated image may be obtained from one or more updated poses.

The at least one updated image may be obtained automatically. For example, the imaging device may continuously obtain images subsequent to the set of images. In another example, the imaging device may obtain images at a time interval. In other embodiments, the at least one updated image may be obtained when a user such as a surgeon or other medical provider inputs instructions for the imaging device to obtain the at least one updated image. In such embodiments, the user may, for example, wish to confirm a pose of an anatomical element, or may be aware of a shift or change to an anatomical element and may wish to update the three-dimensional representation with such new information.

In embodiments where a pose, position, orientation, size, or shape of an anatomical element is to be confirmed, the at least one updated image may be compared to corresponding image(s) of the set of images. In such embodiments, the at least one updated image may be obtained from at least one of the one or more poses. Comparing the at least one updated image and the corresponding image(s) of the set of images may comprise aligning the at least one updated image and the corresponding image(s) of the set of images and detecting any changes between the images. In such embodiments, the at least one updated image and the corresponding image(s) of the set of images may be obtained from the imaging device at the same pose. In other embodiments, at least one updated image and the corresponding image(s) of the set of images may be obtained from different poses. In such embodiments, the one or more anatomical elements depicted in the at least one update image may be aligned with the one or more anatomical elements depicted in corresponding image(s) of the set of images and changes may be detected between one or more anatomical elements depicted in the images.

The method 500 also comprises receiving updated pose information (step 508). The step 508 may be the same as or similar to the step 412 of the method 400 described above.

The method 500 also comprises inputting the at least one updated image and the updated pose information to a reconstruction model (step 512). The step 512 may be the same as or similar to the step 420 of the method 400 described above. The reconstruction model may be the same as or similar to the reconstruction model 206, 125. In some embodiments, generating the updated three-dimensional representation may comprise replacing at least one image of the one or more images with the at least one updated image.

For example, where a change in the one or more anatomical elements is detected such as in, for example, step 504, at least one image of the one or more set of images may be replaced with the at least one updated image. In other embodiments, at least one image of the one or more set of images may be replaced with the at least one updated image regardless of whether a change is detected. In still other embodiments, when a change is not detected, the at least one image of the one or more set of images may not be replaced with the at least one updated image. In such embodiments, the at least one updated image may be saved to, for example, a memory such as the memory 106, or discarded.

The method 500 also comprises receiving, from the reconstruction model, an updated three-dimensional representation of the one or more anatomical elements (step 516). The step 516 may be the same as or similar to the step 420 of the method 400 described above. The updated three-dimensional representation may include new information about a pose, size, shape, position, or orientation of the one or more anatomical elements.

It will be appreciated that in some embodiments, the steps 505, 508, and/or 512 may be continuously repeated to provide updates regarding a pose, position, orientation, size, or shape of the one or more anatomical elements. In other words, at least one updated image may be obtained continuously, and in some instances, the subsequent updated image(s) may be inputted into the reconstruction model to continuously generate an updated three-dimensional representation of the one or more anatomical elements.

The present disclosure encompasses embodiments of the method 500 that comprise more or fewer steps than those described above, and/or one or more steps that are different than the steps described above.

It will be appreciated that any of the steps of methods 300, 400, and/or 500 may be combined in any order. For example, some steps of method 400 and some steps of method 500 may be combined and executed. As noted above, the present disclosure encompasses methods with fewer than all of the steps identified in FIGS. 3-5 (and the corresponding description of the methods 300, 400, 500), as well as methods that include additional steps beyond those identified in FIGS. 3-5 (and the corresponding description of the methods 300, 400, 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for reconstructing a three-dimensional representation comprising:
  an imaging device that captures images using a first imaging modality;
  a processor; and
  a memory storing data for processing by the processor, the data, when processed, causing the processor to:
   orient the imaging device at one or more poses;
   receive an intraoperative image from the image device at each of the one or more poses to form a set of intraoperative images, the set of intraoperative images depicting one or more anatomical elements;

receive pose information at each of the one or more poses;

input the set of intraoperative images and the pose information to a reconstruction model, the reconstruction model configured to generate a three-dimensional representation of the one or more anatomical elements based on the set of intraoperative images, the pose information, and a preoperative image of the one or more anatomical elements captured using a second imaging modality different than the first imaging modality;

receive, from the reconstruction model, the three-dimensional representation of the one or more anatomical elements; and generate instructions for navigating at least one instrument based on the three-dimensional representation of the one or more anatomical elements.

2. The system of claim 1, wherein the set of intraoperative images comprise one or more two-dimensional images.

3. The system of claim 1, further comprising a navigation system configured to track at least the imaging device, wherein the pose information is received from the navigation system.

4. The system of claim 1, wherein the first imaging modality is an ultrasound imaging modality.

5. The system of claim 4, wherein the second imaging modality is a CT or MRI imaging modality.

6. The system of claim 1, wherein the memory stores further data for processing by the processor that, when processed, causes the processor to:

receive at least one updated intraoperative image;

receive updated pose information corresponding to the at least one updated intraoperative image;

input the at least one updated intraoperative image and the updated pose information to the reconstruction model, the reconstruction model configured to generate an updated three-dimensional representation of the one or more anatomical elements based on the at least one updated intraoperative image and the updated pose information; and receive, from the reconstruction model, an updated three-dimensional representation of the one or more anatomical elements.

7. The system of claim 6, wherein generating the updated three-dimensional representation comprises replacing at least one intraoperative image of the set of intraoperative images with the at least one updated intraoperative image.

8. The system of claim 6, wherein the at least one updated intraoperative image is obtained for at least one of the one or more poses.

9. The system of claim 6, wherein the at least one updated intraoperative image is obtained at one or more updated poses.

10. The system of claim 1, wherein the memory stores further data for processing by the processor that, when processed, causes the processor to receive the preoperative image and preoperative pose information, and wherein generating the three-dimensional representation is additionally based on the preoperative pose information.

11. The system of claim 10, wherein the reconstruction model is training using at least one of historical sets of images, historical pose information, and historical preoperative images.

12. The system of claim 10, wherein the imaging device is oriented by at least one robotic arm, and wherein the pose information is obtained from the at least one robotic arm.

13. The system of claim 1, wherein the memory stores further data for processing by the processor that, when processed, causes the processor to:

segment at least one of the one or more anatomical elements from the three-dimensional representation to yield at least one segmented anatomical element; and track the at least one segmented anatomical element.

14. A device for reconstructing a three-dimensional representation comprising:

a processor; and a memory storing data for processing by the processor, the data, when processed, causing the processor to:

orient an imaging device at one or more poses, the imaging device capturing images using a first imaging modality;

receive an intraoperative image at each of the one or more poses to form a set of intraoperative images, the set of intraoperative images depicting one or more anatomical elements;

receive pose information at each of the one or more poses;

input the set of intraoperative images and the pose information to a reconstruction model, the reconstruction model configured to generate a three-dimensional representation of the one or more anatomical elements based on the set of intraoperative images, the pose information, and a preoperative image of the one or more anatomical elements captured using a second imaging modality different than the first imaging modality;

receive, from the reconstruction model, the three-dimensional representation of the one or more anatomical elements; and generate instructions for navigating at least one instrument based on the three-dimensional representation of the one or more anatomical elements.

15. The device of claim 14, wherein the memory stores further data for processing by the processor that, when processed, causes the processor to:

receive at least one updated intraoperative image;

receive updated pose information corresponding to the at least one updated intraoperative image;

input the at least one updated intraoperative image and the updated pose information to the reconstruction model, the reconstruction model configured to generate an updated three-dimensional representation of the one or more anatomical elements based on the at least one updated intraoperative image and the updated pose information; and receive, from the reconstruction model, an updated three-dimensional representation of the one or more anatomical elements based on the at least one updated intraoperative image and the updated pose information.

16. The device of claim 15, wherein generating the updated three-dimensional representation comprises replacing at least one intraoperative image of the set of intraoperative images with the at least one updated intraoperative image.

17. The device of claim 15, wherein the at least one updated intraoperative image is obtained for at least one of the one or more poses.

18. The device of claim 15, wherein the at least one updated intraoperative image is obtained at one or more updated poses.

19. A system for reconstructing an image comprising:

an imaging device that captures images using a first imaging modality;

a navigation system;
a processor; and
a memory storing data for processing by the processor, the data, when processed, causing the processor to:
  orient the imaging device at one or more poses;
  receive an intraoperative image at each of the one or more poses to form a set of intraoperative images, the set of intraoperative images depicting one or more anatomical elements;
  receive pose information at each of the one or more poses from the navigation system;
  input the set of intraoperative images and the pose information to a reconstruction model, the reconstruction model configured to generate a three-dimensional representation of the one or more anatomical elements based on the set of intraoperative images, the pose information, and a preoperative image of the one or more anatomical elements captured using a second imaging modality different than the first imaging modality;
  receive, from the reconstruction model, the three-dimensional representation of the one or more anatomical elements; and
  generate instructions for navigating at least one instrument based on the three-dimensional representation of the one or more anatomical elements.

* * * * *